(12) United States Patent
Davies (10) Patent No.: US 11,813,276 B2
(45) Date of Patent: Nov. 14, 2023

(54) COMPOSITIONS AND METHODS FOR THE TREATMENT OF AUD

(71) Applicant: University of Southern California, Los Angeles, CA (US)

(72) Inventor: Daryl Davies, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/507,507

(22) Filed: Oct. 21, 2021

(65) Prior Publication Data

US 2022/0125816 A1 Apr. 28, 2022

Related U.S. Application Data

(60) Provisional application No. 63/104,719, filed on Oct. 23, 2020.

(51) Int. Cl.
| | | |
|---|---|---|
| *A61K 31/7048* | (2006.01) | |
| *A61P 25/32* | (2006.01) | |
| *A61K 31/365* | (2006.01) | |
| *A61K 31/4725* | (2006.01) | |

(52) U.S. Cl.
CPC ........ *A61K 31/7048* (2013.01); *A61K 31/365* (2013.01); *A61K 31/4725* (2013.01); *A61P 25/32* (2018.01)

(58) Field of Classification Search
CPC .............. A61K 31/7048; A61K 31/365; A61K 31/4725; A61P 25/32

USPC ......................................................... 514/30
See application file for complete search history.

(56) References Cited

PUBLICATIONS

Ballent et al. (DMD 34:457-463, 2006).*
Kannan et al. (ACS Chem. Neurosci. (2011), 2, 82-89; Published on Web Date: Oct. 21, 2010).*
Ray (U.S. National Library of Medicine; ClinicalTrials.gov; Aug. 8, 2018).*
Silva et al. A novel pharmacotherapy approach using P-glycoprotein (PGP/ABCB1) efflux inhibitor combined with ivermectin to reduce alcohol drinking and preference in mice. Alcohol 86 (2020) 1-8, Available online Apr. 8, 2020. (Year: 2020).*
Roche et al., "A Pilot Study of the Safety and Initial Efficacy of Ivermectin for the Treatment of Alcohol Use Disorder", Alcoholism: Clinical and Experimental Research, Jun. 2016, vol. 40, No. 6, pp. 1312-1320.

* cited by examiner

*Primary Examiner* — Yih-Horng Shiao
(74) *Attorney, Agent, or Firm* — Foley & Lardner LLP (57) ABSTRACT

Provided herein are methods to improve transport or uptake of an avermectin compound in a cell or tissue expressing an efflux transporter P-glycoprotein (Pgp) by co-administering an effective amount of the avermectin compound and a Ppg inhibitor to the cell or tissue. The method also provides improved efficiency transport or uptake of an avermectin compound in the cell or tissue. The methods can be used therapeutically to treat Alcohol Use Disorder.

8 Claims, 7 Drawing Sheets

COMPOSITIONS AND METHODS FOR THE TREATMENT OF AUD

CROSS-REFERENCE TO RELATED APPLICATION

This application claims priority to U.S. Provisional Application No. 63/104,719, filed Oct. 23, 2020, the entire contents of which is incorporated by reference in its entirely into the present application.

STATEMENT OF GOVERNMENT SUPPORT

This invention was made with government support under AA022448 awarded by National Institutes of Health. The government has certain rights in the invention.

BACKGROUND

Alcohol Use Disorder (AUD) has a major national impact by affecting over 18 million people, causing approximately 88,000 deaths and costing upward of $220 billion annually in the United States alone. Unfortunately, FDA-approved AUD pharmaceuticals are few and mostly ineffective in patients suffering AUD. Therefore, the identification of novel targets and/or novel methods for the development of effective medications represents a critical public health need.

SUMMARY OF THE DISCLOSURE

The altered function or expression of central nervous system (CNS) genes has long been considered a significant factor in contributing to the behavioral phenotype of alcoholism. By profiling gene expression in rodent strains undergoing multiple drinking paradigms, researchers have begun to identify potential candidate genes and pathways that may impart novel mechanistic information that drives the neurobiology of alcoholism. It is reported that P2X4 receptors (P2X4Rs) play a role in the regulation of ethanol intake and that positive modulation of P2X4Rs by two avermectin compounds (ivermectin [IVM] and moxidectin [MOX]) significantly reduced ethanol intake in male and female mice. Moreover, chronic administration of IVM or MOX did not significantly alter the reduction of ethanol intake (i.e., no tolerance to IVM) nor was any measured or observed obvious increase in toxicity or addictive liabilities by IVM or MOX in the disclosed ethanol drinking studies.

DETAILED DESCRIPTION

Throughout this disclosure, various publications, patents and published patent specifications are referenced by an identifying citation. Several references are referenced by an Arabic number, and the complete citation for is found preceding the claims in the References section of this disclosure. The disclosures of these publications, patents and published patent specifications are hereby incorporated by reference into the present disclosure in their entirety to more fully describe the state of the art to which this invention pertains.

Definitions

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, $2^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

An animal, subject or patient for diagnosis, treatment, or administration of the compounds if the disclosure thereto, refers to an animal such as a mammal, or a human, ovine, bovine, feline, canine, equine, simian, etc. Non-human animals subject to diagnosis, treatment, or administration thereto of compounds of the disclosure include, for example, simians, murine, such as, rat, mice, canine, leporid, livestock, sport animals, and pets.

A "composition" "pharmaceutical composition" as used herein, intends an active agent, such as a compound as disclosed herein and a carrier, inert or active. The carrier can be, without limitation, solid such as a bead or resin, or liquid, such as phosphate buffered saline.

Administration or treatment in "combination" refers to administering two agents such that their pharmacological effects are manifest at the same time. Combination does not require administration at the same time or substantially the same time, although combination can include such administrations.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zürich, Switzerland), for a discussion of pharmaceutical salts, their selection, preparation, and use.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

A solvate of a compound is a solid-form of a compound that crystallizes with less than one, one or more than one molecules of a solvent inside in the crystal lattice. A few examples of solvents that can be used to create solvates, such as pharmaceutically acceptable solvates, include, but are not limited to, water, C1-C6 alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

An "effective amount" is an amount sufficient to effect beneficial or desired results. An effective amount can be administered in one or more administrations, applications or dosages and is determined by the system in which the drug or compound is delivered, e.g., an effective amount for in vitro purposes is not the same as an effective amount for in vivo purposes. For in vivo purposes, the delivery and "effective amount" is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prevention.

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

"Affinity label" as used herein refers to a compound, that may be appended to a protein or another compound so that the protein or other compound can be purified from its crude source using an affinity purification technique, for example affinity chromatography, wherein the purification processes selects for the affinity label and the protein or other compound appended thereto based on the label's interactions with an affinity matrix used for the purification. These interactions include, but are not limited to, antigen-antibody interactions, enzyme-substrate interactions, receptor-ligand interactions, hydrogen bonding, ionic interactions or electrostatic interactions. Non-limiting examples of affinity labels include chitin binding protein (CBP), maltose binding protein (MBP), Strep-tag, glutathione-S-transferase (GST), poly(His) tags, NE-tag, Spot-tag, albumin-binding protein (ABP), alkaline phosphatase (AP), AU epitopes, bacteriophage T7 or V5 epitope, HSV epitope, biotin-carboxy carrier protein, biotin, and bluetongue virus tag (B-tag). Non limiting examples of matrices include, but are not limited to, albumin/low pH, mAb/low pH, avidin or streptavidin/biotin or denaturation, calmodulin/EGTA or EGTA and high salt, chloramphenicol/chloramphenicol, chitin, choline, methotrexate/folate, galactose, glutathione, and a divalent metal.

As used herein, the term "contacting" intends bringing the reagents into close proximity with each other so that a chemical or biochemical reaction can occur among the reagents. In one aspect, the term intends admixing the components, either in a reaction vessel or on a plate or dish. In another aspect, it intends in vivo administration to a subject.

The term "binding" or "binds" as used herein are meant to include interactions between molecules that may be covalent or non-covalent which, in one embodiment, can be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment," as used herein, also refers to a peptide chain.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

Modes for Carrying Out the Disclosure

Applicant hypothesized that lipophilic nature of avermectin compounds suggested that they should readily pass the blood brain barrier (BBB) and that they also are good substrates for the efflux transporter P-glycoprotein (Pgp/

ABCB1). As such, the doses of IVM or MOX and the long time from administration of IVM (8 hours) or MOX (4 hours) to time of significant reduction of ethanol intake is not ideal. Applicant provides herein a novel approach that targets an efflux activity of Pgp where Pgp which significantly that reduces the bioavailability of the avermectin to the CNS targets (e.g. P2X4Rs)—a contributor resulting in the reduced CNS bioavailability of IVM or MOX. Applicant's work is directed to methods and composition that inhibit Pgp to result in an increase avermectin penetration of the BBB, resulting in shorter time intervals for IVM to reach therapeutic concentrations in the CNS with lower dosing.

Thus, in one aspect provided herein is a method to improve transport or uptake of an avermectin compound in a cell or tissue expressing the efflux transporter P-glycoprotein (Pgp/ABCB1) the method comprising, or consisting essentially of, or yet further consisting of co-administering an effective amount of the avermectin compound and a Ppg inhibitor to the cell or tissue. In one aspect, the compounds and/or inhibitor are detectably labeled.

Also provided is a method to improve efficiency transport or uptake of an avermectin compound in a cell or tissue expressing efflux transporter P-glycoprotein (Pgp/ABCB1), the method comprising, or consisting essentially of, or yet further consisting of, co-administering an effective amount of the avermectin compound and a Ppg inhibitor to the cell or tissue. In one aspect, the compounds and/or inhibitor are detectably labeled.

The contacting can be in vitro or in vivo. When in vitro, the method is useful to assay or test for effective amounts or combination therapies. When in vivo, the method is practiced in an animal such as a mouse or rat, it is useful to test effective amounts or combination therapies. When practiced in vivo in a human, it is useful therapeutically. In one aspect, the cell or tissue is mammalian cell or tissue such as a human cell or tissue.

Also provided herein are methods to treat Alcohol Use Disorder (AUD) in a subject in need thereof, comprising or consisting essentially of, or yet further consisting of co-administering an effective amount of an avermectin compound and a Ppg inhibitor to the subject, thereby treating AUD. The subject can be a mammal, such as a human patient suffering from AUD.

Non-limiting examples of avermectin compounds for use in the methods are ivermectin (IVM) and moxidectin (MOX). A non-limiting example of a Ppg inhibitor for use in the methods comprise tariquidar.

The avermectin compound and the Ppg inhibitor can be administered or contacted with the cell or tissue sequentially or serially and they can be administered in one or more administrations or doses. When administered to an animal or human, they can be administered by any effective local or system route, e.g., orally or intravenously.

Further provided herein is a composition comprising a therapeutically effective amount of an avermectin compound and a Ppg inhibitor. Non-limiting examples of avermectin compounds are ivermectin (IVM) and moxidectin (MOX). A non-limiting example of a Ppg inhibitor comprises tariquidar. The compositions can further comprise a carrier, such as a pharmaceutically acceptable carrier. They can be further processed, e.g. frozen or lyophilized for ease of storage and transport. Thus, they may further comprise buffers, stabilizers, surfactants and the like.

Further provided herein is a kit comprising, or consisting essentially of, or yet further consisting of an avermectin compound and a Ppg inhibitor. Non-limiting examples of avermectin compounds include ivermectin (IVM) or moxidectin (MOX). A non-limiting example of a Ppg inhibitor comprises tariquidar. The kits can further comprise instructions for use, e.g., instructions are for use in any one of the methods as disclosed herein.

The pharmaceutical compositions for the administration of the compounds can be conveniently presented in dosage unit form and can be prepared by any of the methods well known in the art of pharmacy. The pharmaceutical compositions can be, for example, prepared by uniformly and intimately bringing the compounds provided herein into association with a liquid carrier, a finely divided solid carrier or both, and then, if necessary, shaping the product into the desired formulation. In the pharmaceutical composition the compound provided herein is included in an amount sufficient to produce the desired therapeutic effect. For example, pharmaceutical compositions of this disclosure may take a form suitable for virtually any mode of administration, including, for example, topical, ocular, oral, buccal, systemic, nasal, injection, infusion, transdermal, rectal, and vaginal, or a form suitable for administration by inhalation or insufflation.

For topical administration, the compounds can be formulated as solutions, gels, ointments, creams, suspensions, etc., as is well-known in the art.

Systemic formulations include those designed for administration by injection (e.g., subcutaneous, intravenous, infusion, intramuscular, intrathecal, or intraperitoneal injection) as well as those designed for transdermal, transmucosal, oral, or pulmonary administration.

Useful injectable preparations include sterile suspensions, solutions, or emulsions of the compounds provided herein in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the compounds provided herein can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the compounds provided herein in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques well known to the skilled artisan. The pharmaceutical compositions of the technology may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

The compounds and compositions of the present invention are also useful in the preparation of medicaments. The methods and techniques for preparing medicaments of a composition are known in the art. For the purpose of illustration only, pharmaceutical formulations and routes of delivery are detailed herein.

Thus, one of skill in the art would readily appreciate that any one or more of the compositions described above, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the disclosure.

Two Bottle Choice Study Methods:

One tube contained tap water and the other a 10% ethanol solution (10E) in tap water. Mice were given free access to 10E with bottle positions alternated every other day. Fresh fluids were provided twice a week when cages were changed. Body weights were recorded daily. Every morning daily fluid intake (to the nearest 0.1 ml) was recorded from both bottles by measuring the level of the meniscus on the graduated drinking tube. Daily 10E intake was measured until it stabilized (±10% variability from the mean dose of the last 3 days). After establishing stable alcohol drinking levels, mice received daily saline injections (intraperitoneal; i.p.) until 10E intake stabilized (which averaged between 4 and 5 days of saline injections). In all cases, injections were administered immediately prior to the period of 24 h access to 10E versus tap water, so that the change in thinking over 24 h after IVM and TQ administration was measured. Mice then received either IVM (0.5-2 mg/kg), TQ (10 mg/kg), (0.5-2 mg/kg) and TQ (10 mg/kg; 30 min. prior to IVM), or saline (control for injection effect) once per week. Animals were not injected on subsequent days until 10E drinking stabilized at baseline levels, and then mice were injected with another dose of IVM. Consumption of 10E returned to baseline levels prior to the administration of each subsequent dose of IVM tested.

Additional embodiments are provided in the attached Appendix, incorporated herein by reference.

Figure 1A:
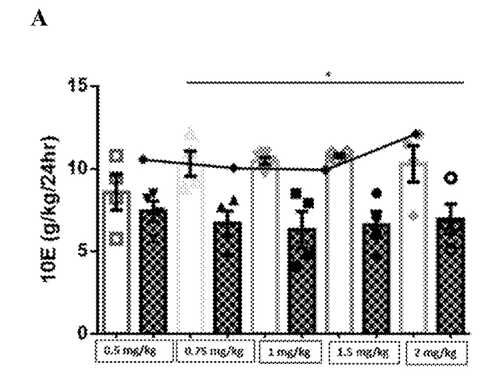
FIGS. 1A-1C show ivermectin and tariquidar co-administration significantly reduces ethanol intake and ethanol preference in C57BL/5J mice. A) Average intake of g/kg ethanol per day for five IVM dose (clear) or IVM co-administered with 10 mg/kg TQ (checkered) against the saline averages (black line). B) Average preference for 10% ethanol for IVM doses (clear bars), IVM+10 mg/kg TQ (checkered), and saline controls (black line). C) The effects of IVM (clear), IVM+10 mg/kg TQ (checkered), TQ, and saline (Ctl) on total fluid intake is presented in panel C. Values represent the mean±SEM for 5 mice per group. *$P<0.05$ versus respective IVM condition, Bonferroni's post-hoc test.
Figure 1B:
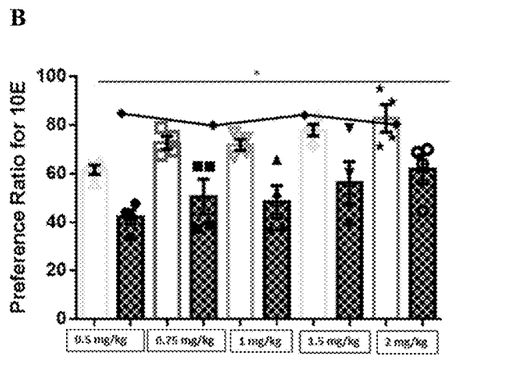
Figure 1C:
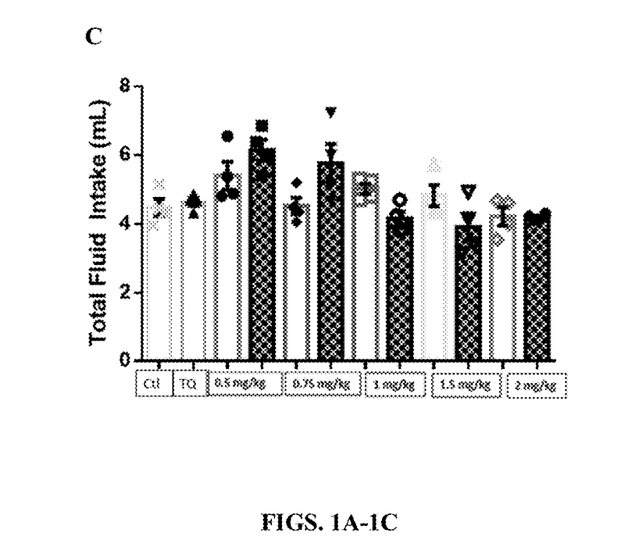
Figure 2:
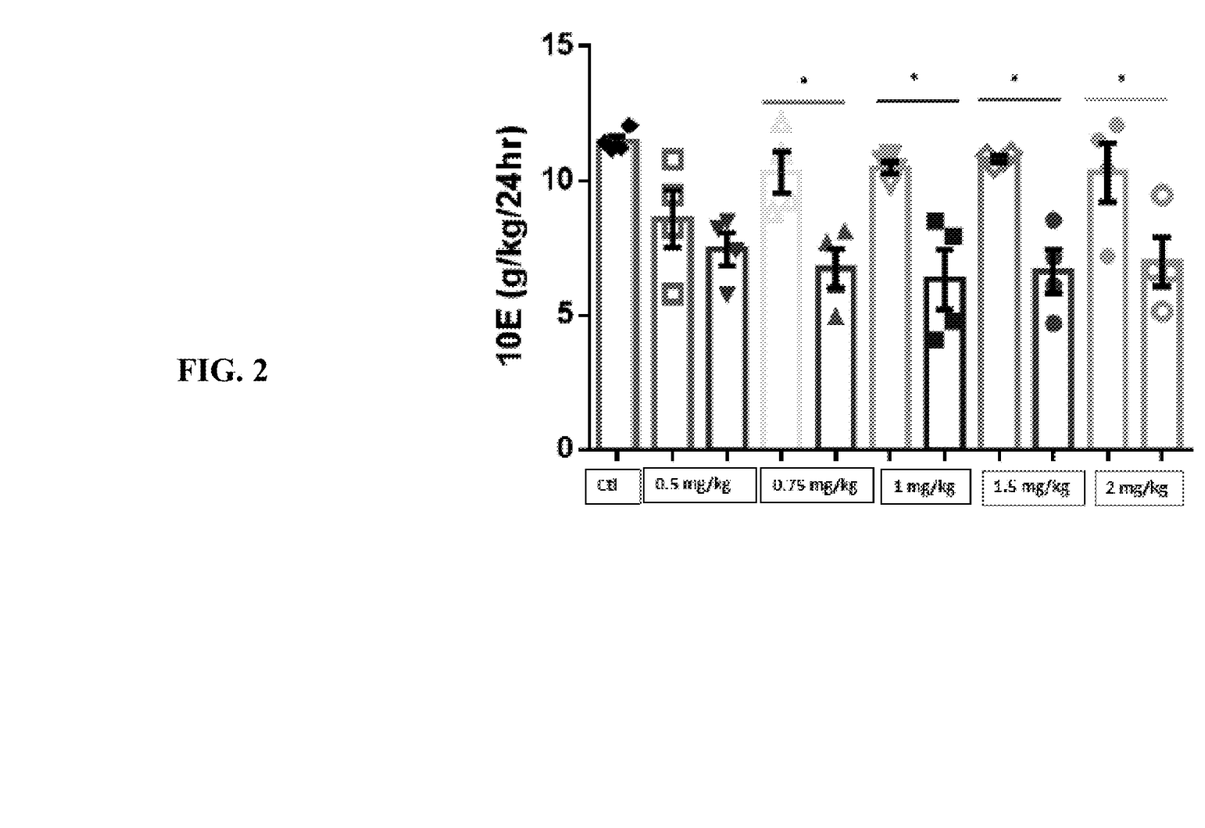
FIG. 2 also shows the benefit of the claimed invention.
Figure 3:
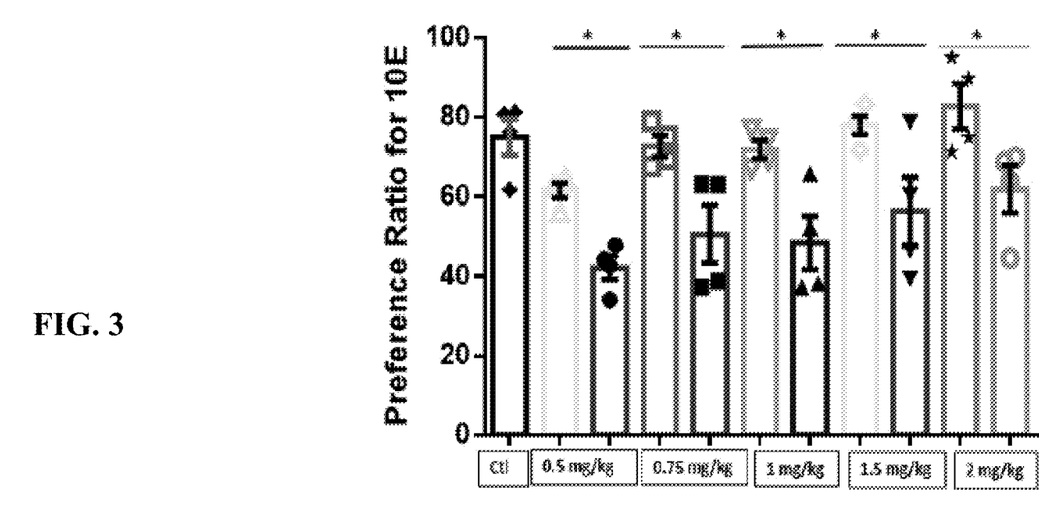
FIG. 3 also shows the benefit of the claimed invention.
Figure 4:
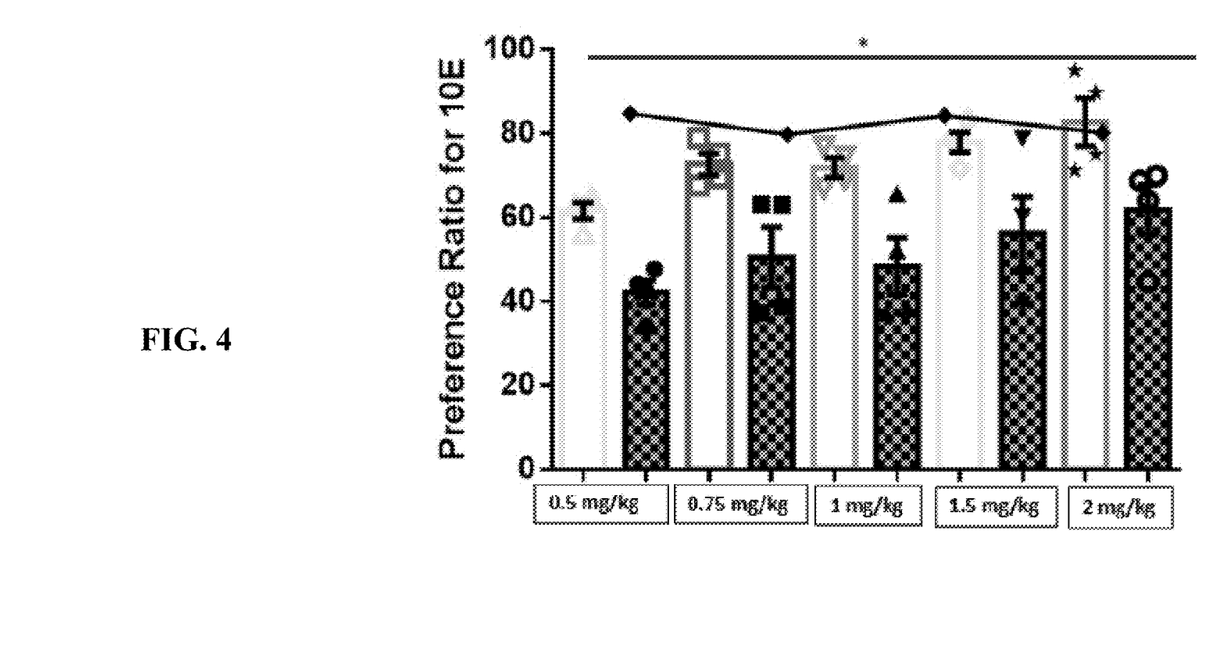
FIG. 4 also shows the benefit of the claimed invention.
Figure 5:
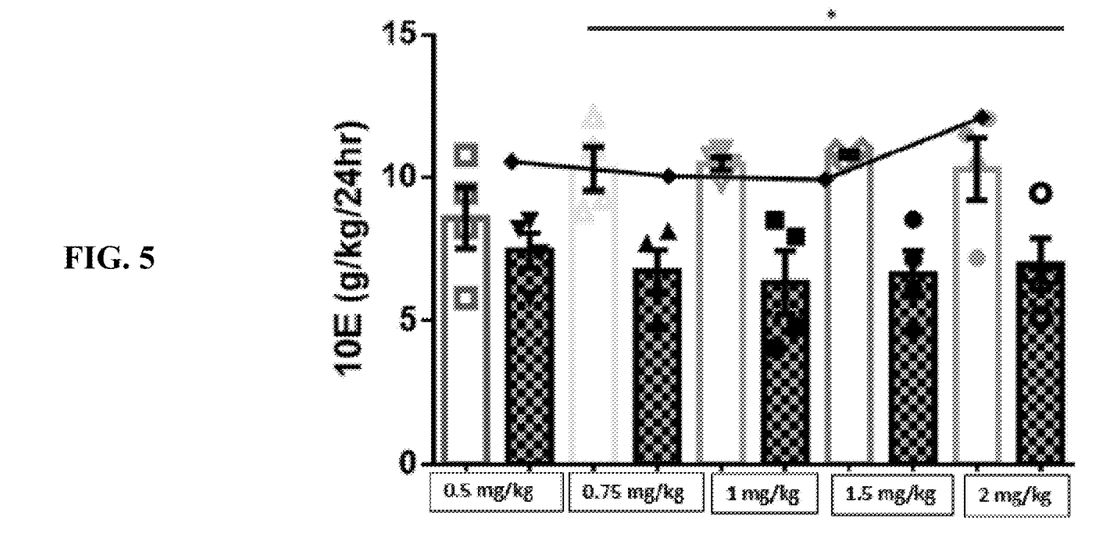
FIG. 5 also shows the benefit of the claimed invention.
Figure 6:
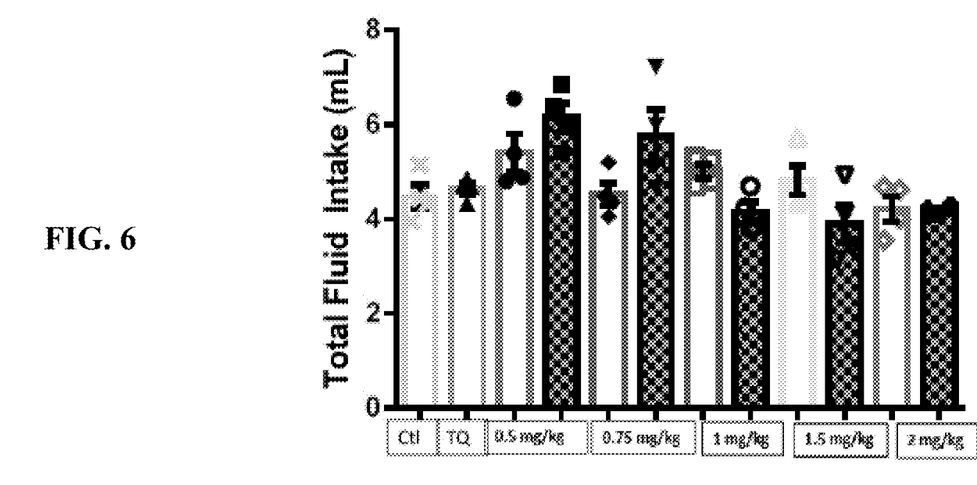
FIG. 6 also shows the benefit of the claimed invention.
Figure 7:
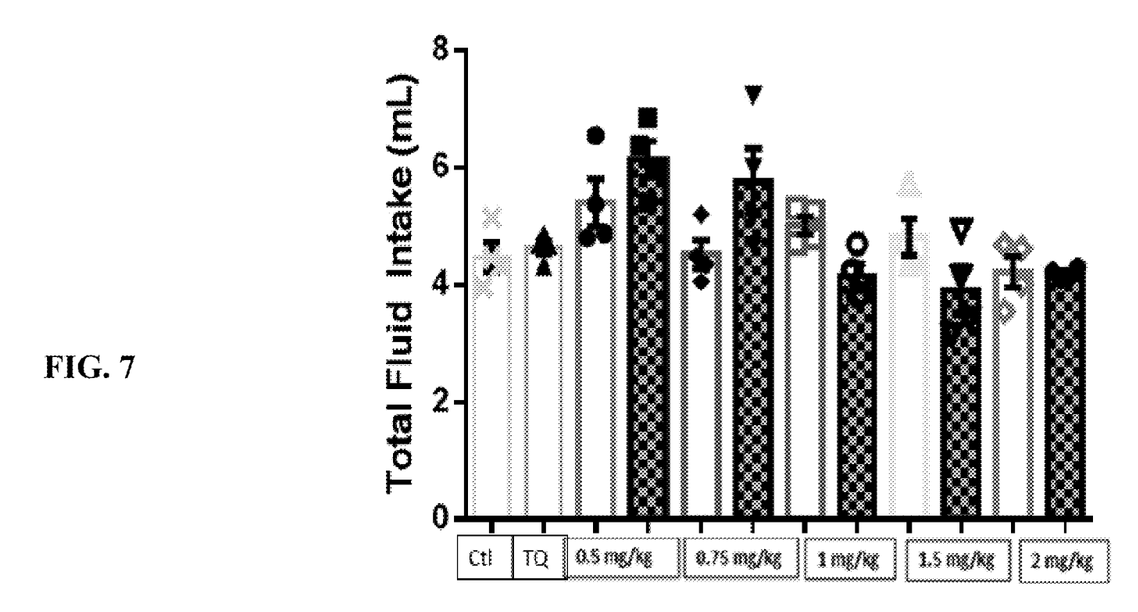
FIG. 7 also shows the benefit of the claimed invention.

Results and Discussion:

To begin this investigation on the utility of Pgp inhibition on IVM efficacy, we conducted a two-bottle choice paradigm to evaluate the preference and voluntary consumption of ethanol using C57BL/6J mice co-administered a single dose IVM and tariquidar (TQ), a third generation Pgp specific inhibitor (FIG. 1). Our lab has previously identified that doses of IVM between 2.5 mg/kg and 10 mg/kg displayed a significant reduction in the voluntary ethanol intake in mice models (Yardlet et al., 2012). By inhibiting Pgp with the co-administration of TQ, we found similar significant reductions in voluntary ethanol intake *($p<0.05$; FIG. 1A) and ethanol preference (*$p<0.01$; FIG. 1B) relative to single ivermectin doses below 2.5 mg/kg. Therefore, by selectively targeting and blocking the efflux activity of Pgp, IVM is highly effective in reducing ethanol drinking behavior at lower doses. As previously reported, the administration of tariquidar with IVM has been shown to result in an accumulation of IVM in the CNS relative to other tissues in C57BL/6J mice (Thoeringer et al., 2007). This accumulation of IVM in the CNS, and increased retention time, can potentially enhance the exposure and modulation of P2X4Rs in the CNS, resulting in the observed changes in ethanol drinking behavior. However, current studies are underway to confirm the TQ-mediated changes in IVM concentrations and retention time in brain tissue.

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. Throughout this disclosure, various publication are referenced by a citation, the full bibliographic citation for each are provided immediately preceding the claims.

What is claimed is:

1. A method to alleviate Alcohol Use Disorder (AUD) in a subject in need thereof, comprising co-administering an effective amount of an avermectin compound and an effective amount of a second P-glycoprotein (Pgp) inhibitor to the subject, thereby alleviating AUD.

2. The method of claim 1, wherein the subject is a mammal.

3. The method of claim 2, wherein the mammal is a human.

4. The method of claim 1, wherein the avermectin compound comprises ivermectin (IVM) or moxidectin (MOX).

5. The method of claim 1, wherein the second Pgp inhibitor comprises tariquidar.

6. The method of claim 1, wherein the avermectin compound and the second Ppg inhibitor are administered sequentially or serially.

7. The method of claim 1, wherein the co-administration is effected in one or more doses.

8. The method of claim 1, wherein the co-administration is orally or intravenously.

* * * * *